US00PP26413P3

(12) United States Plant Patent
Ortiz et al.

(10) Patent No.: US PP26,413 P3
(45) Date of Patent: Feb. 16, 2016

(54) BLACKBERRY PLANT NAMED 'AMARA'

(50) Latin Name: *Rubus rubus*
Varietal Denomination: Amara

(71) Applicant: Hortifrut S.A., Santiago (CL)

(72) Inventors: Maria Pilar Banados Ortiz, San Fernando (CL); Alejandra Andrea Salgado Rojas, Santiago (CL); John Reuben Clark, Fayetteville, AR (US)

(73) Assignee: Hortifrut, S.A., Santiago (CL)

( * ) Notice: Subject to any disclaimer, the term of this patent is extended or adjusted under 35 U.S.C. 154(b) by 77 days.

(21) Appl. No.: 13/986,900

(22) Filed: Jun. 14, 2013

(65) Prior Publication Data

US 2014/0373228 P1 Dec. 18, 2014

(51) Int. Cl.
*A01H 5/00* (2006.01)
*A01H 5/08* (2006.01)

(52) U.S. Cl.
USPC ..... Plt./203
CPC ..... *A01H 5/0887* (2013.01)

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP11,865 | P2 | 5/2001 | Clark et al. |
| PP15,788 | P2 | 6/2005 | Clark et al. |
| PP16,989 | P3 | 8/2006 | Clark et al. |
| PP22,449 | P3 | 1/2012 | Clark |
| 2012/0151645 | P1 | 6/2012 | Clark et al. |

OTHER PUBLICATIONS http://www.freshfruitportal.com/2013/04/29/chile-releases-two-creeping-blackberry-varieties/?country=united%20states.*
"Blackberry—Reuben—Hargreaves Plants", http://reubenblackberry.com, downloaded Oct. 25, 2012, 3 pages.
Clark, John R. et al., "'APF-45' Primocane-fruiting Blackberry," HortScience 46(4): 670-673, 2011.
Clark, John, "Primocane-fruiting Blackberry Breeding," HortScience vol. 43(6), pp. 1637-1639, Oct. 2008.
Clark, John R. et al., "'Prime-Jan' ('APF-8') and 'Prime Jim' ('APF-12') Primocane-fruiting Blackberries", HortScience 40(3): 852-855, 2005.

* cited by examiner

*Primary Examiner* — Annette Para
(74) *Attorney, Agent, or Firm* — King IP Law; Joshua King

(57) ABSTRACT

A new and distinct cultivar of Blackberry plant named 'Amara' as described and shown herein. 'Amara' has a primocane fruiting habit on a thornless plant, coupled with high fruit quality (visually attractive with excellent flavor, firmness, and low regression to red drupelets in post harvest).

4 Drawing Sheets

BACKGROUND AND SUMMARY

Blackberries are a well-known, aggregate fruit enjoyed by many throughout the world. One example of an existing, patented blackberry variety is APF-8 (marketed as Prime Jan® blackberry), U.S. Plant Pat. No. 15,788. Another example of an existing blackberry variety is 'Camila', U.S. Plant patent application Ser. No. 13/694,787 filed 4 Jan. 2013. Such varieties both provide fruit on primocanes, but are thorny. Thus, there is a need for a blackberry variety that is thornless yet provides desirable fruit on primocanes.

The present cultivar, 'Amara', provides one or more of these or other characteristics. For example, the present cultivar, 'Amara', is thornless while also providing desirable fruit on primocanes.

Compared to APF-8 based on some typical results, the present cultivar, Amara (also known as "HFM-2"), and APF-8 are both primocane-fruiting blackberries, but Amara is thornless. In addition, the fruits of Amara are considerably firmer and smaller (7.6 g versus 9.8 g, respectively) than those of APF-8. Amara fruits are sweeter than those of APF-8 (10.9° Brix versus 9.8° Brix, respectively). In post-harvest storage, fruits of Amara maintain higher levels of firmness (85% firm at 7 days at 5° C.) than fruits of APF-8 (50% firm at 7 days at 5° C.). Amara fruits also have a lower level of regression to red drupelets (less than 10%) in post-harvest storage (same conditions and time as above observation) than those of APF-8 (20 to 25% regression). The ripening date of primocane fruits of Amara and APF-8 are similar.

Compared to Camila based on some typical results, the present cultivar, Amara (also known as "HFM-2"), and Camila are both primocane-fruiting blackberries, but Amara is thornless. In addition, Amara and Camila have the same maternal parent ('APF-77' cultivar) but Amara has less vegetative vigor and shorter internodes than Camila. Further, Amara begins flowering (on primocanes) about five days before Camila, but Camila takes about 60 days from flower opening to fruit ripening while Amara takes about 75 days, so Amara fruit ripens about ten days after Camila. Fruits of both varieties are broadly oblong in shape, but those of Amara are slightly smaller than the fruits of Camila, averaging 7.6 grams versus 8.4 grams, respectively. Amara fruits are not as sweet as fruits of Camila (10.9° Brix versus 15.1° Brix, on average, respectively), however neither variety has any bitter aftertaste common to other blackberry varieties. Titratable acidity of Amara is also somewhat higher than Camila 0.9% versus 0.7%, respectively. Fruits of Amara are considerably firmer than those of Camila, with 85% and 35% firm fruit, for each variety, respectively, after 7 days at 5° C.

Speaking more generally about blackberry varieties, there are a number of thornless blackberries in existence, but they are not primocane fruiting types. On the other hand, there are some existing primocane-fruiting blackberries, but these are not thornless. Compared to the thorny primocane-fruiting blackberries, Amara is somewhat similar to the variety 'Reuben' (U.S. Plant Pat. No. 23,497) in that both have moderate stature and erect architecture. Of the thornless, floricane-fruiting blackberries, Amara is somewhat similar to the variety 'Ouachita' (U.S. Plant Pat. No. 17,162) in that both fruit on floricanes during the mid-season.

BRIEF DESCRIPTION OF THE PHOTOGRAPHS

Figure 1:
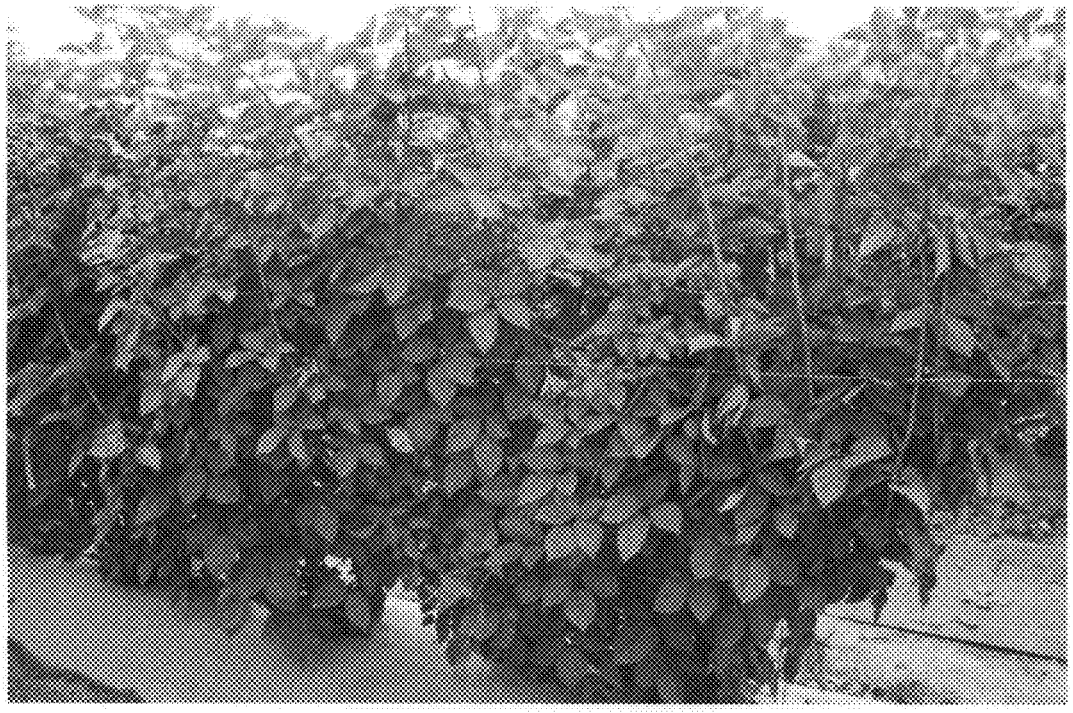
FIG. 1 is a photograph of the whole plant of the Blackberry cultivar 'Amara', showing the thornless stems and general appearance of the plant. The photograph was taken on 16 Apr. 2013, the plants are 12 months old, and are growing in Hualcapo, fifth Region of Valparaiso, Chile.
Figure 2:
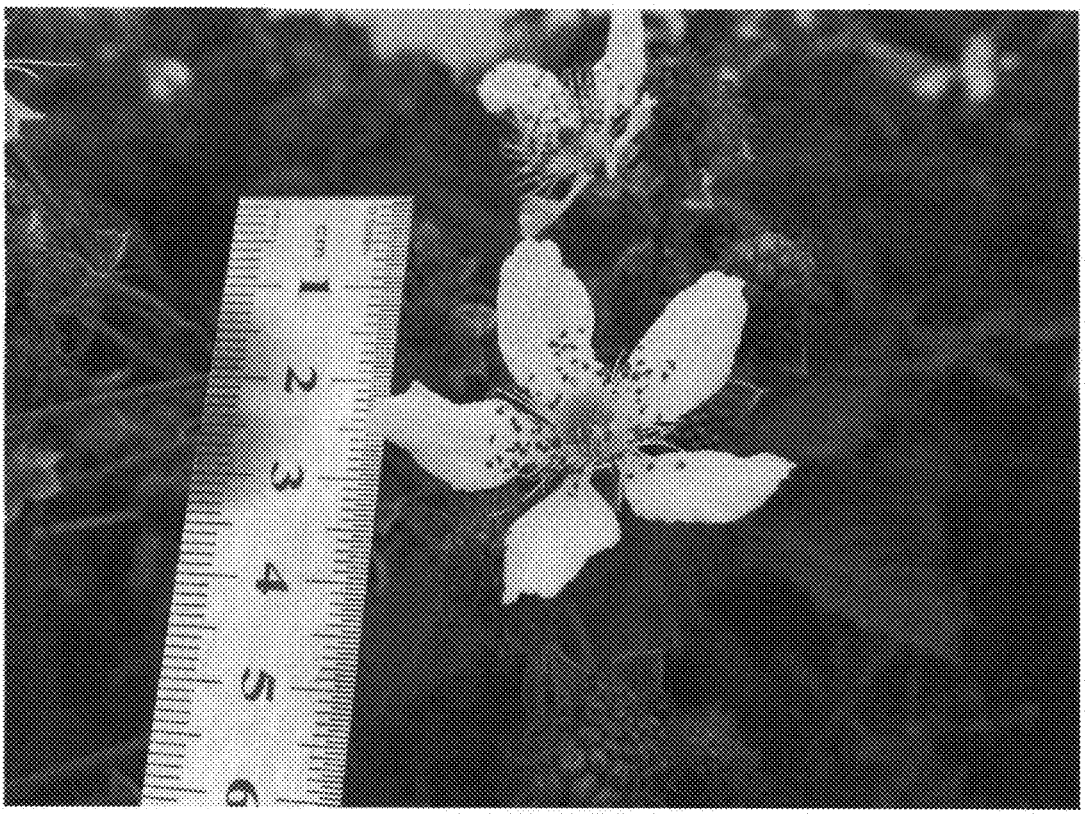
FIG. 2 is a photograph of a flower of the Blackberry cultivar 'Amara'.
Figure 3:
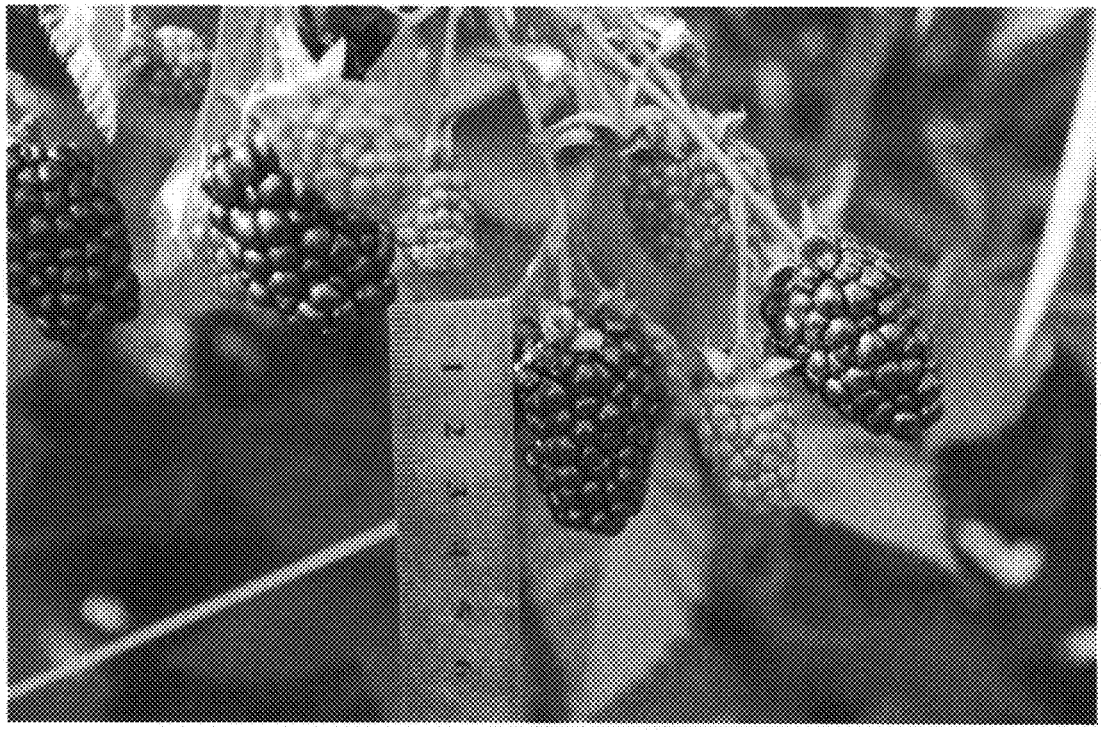

FIG. 3 is a close-up photograph of ripe and unripe fruit on primocanes of the Blackberry cultivar 'Amara'. The photograph was taken on 28 Apr. b 2013. The plants are 12 months old and growing in Hualcapo, fifth Region of Valparaiso, Chile.

Figure 4:
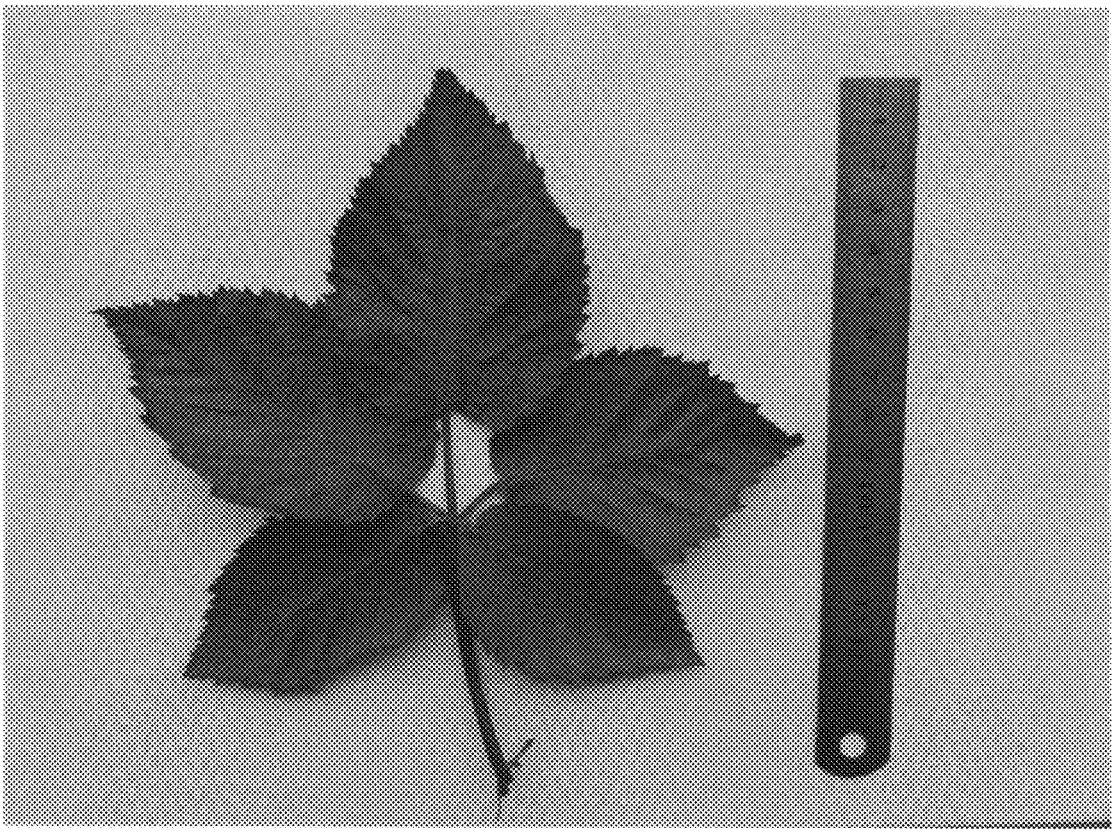

FIG. 4 is a close-up photograph of a leaf detail of the Blackberry cultivar 'Amara'.

DETAILED DESCRIPTION

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown in Chile during the normal Chilean growing season. Data were obtained on plants that were 1-4 years old.

Cultivar name: 'Amara'.

Classification:

*Family.*—Rosaceae.

*Botanical name.*—*Rubus rubus.*

*Common name.*—Blackberry.

Parentage:

*Female parent.*—APF-77. APF-77 is a proprietary cultivar marketed under the trademark Black Magic™. APF-77 is also the subject of U.S. Plant patent application Ser. No. 13/374,444, filed 29 Dec. 2011. Differentiation of Amara from female parent APF-77 (note, APF-77 (and APF-8, discussed above) were evaluated in Arkansas, USA while Amara was evaluated in central Chile): Both APF-77 and Amara are primocane-fruiting blackberry cultivars, but Amara is distinct in that it is thornless, even completely thornless, while APF-77 has thorny stems. Amara and APF-77 bear fruit on floricanes as well as primocanes. It appears that fruits of Amara tend to be sweeter than those of APF-77: in Chile, Amara fruits have an average of 10.9° Brix whereas those of APF-77 in Arkansas have an average of 10.1° Brix. There appears to be a difference in fruit size also, with floricane fruits of APF-77 in Arkansas weighing on average 6 to 7 grams, whereas floricane fruits of Amara weigh only 5.7 g.

*Male parent.*—A-2293T. A-2293T is a proprietary variety but not subject to plant patent. Differentiation of Amara from male parent A-2293T (note, A-2293T was evaluated in Arkansas, USA while Amara was evaluated in central Chile): A-2293T and Amara are both thornless, but A-2293T does not have primocane-fruiting habit, this is the primary difference. In Arkansas, floricane fruits of A-2293T begin ripening slightly earlier than those of APF-8, beginning around 10 and 12 June, respectively. In Chile the floricane fruits of Amara ripen at about the same corresponding time as those of APF-8 grown in Chile, therefore it appears that if Amara and A-2293T were grown in the same environment, then the dates of floricane fruit ripening would also be similar. Floricane fruits of Amara are larger than those of A-2293T: The average weight of floricane fruits are 4.5 g for A-2293T (in Arkansas) and 5.7 g for Amara (in Chile). Soluble solids of Amara and A-2293T appear to be similar, with average values for Amara in Chile being 11.2° Brix and for A-2293T, being 11.0° Brix in Arkansas.

Further information about the new variety Amara:

The cross that created Amara was made in 2006 near Clarksville, Ark., USA. It was a controlled hand pollination of the female APF-77×male A-2293T. Seeds of this cross were sent to Chile in September 2006 and were planted in a nursery in Hijuelas, 5th Region of Valparaiso, Chile. The seedlings were then planted in Nogales (32° 44' 39.9"S.; 71° 10'30.4"W.), 5th region of Valparaiso in December 2007 and January 2008. The first evaluation of the seedlings of this cross was made during the southern hemisphere summer of December 2008 to March 2009. The Age of plants used for the photographs in the Figures: 12 months.

References to color refer to The R.H.S. Colour Chart—Fifth Edition.

The first asexual reproduction of Amara occurred in 2010 when tissue cultures of Amara were established in vitro with whole-bud explants from primocanes (vegetative shoots) in a tissue culture lab in Macul, Santiago, Chile. About 100 plantlets were successfully propagated and acclimatized by this micropropagation method. In 2012, fifty plantlets from micropropagation were planted in a trial plot in Hualcapo, fifth Region of Valparaiso, Chile. No off types have been observed to date.

Amara was first selected in December 2008 in the variety garden at Nogales, Fifth Region of Valparaiso, Chile. The selection was made based on Amara's high floricane fruit quality (good flavor, attractive appearance, and high firmness) combined with lack of undesirable thorns. In later evaluations, it was seen that the primocane fruits of Amara share the good traits observed on the floricane fruits. After first being selected based on floricane fruiting habit, Amara was cut to the ground each winter (thereby eliminating any floricanes or floricane fruits) so floricane fruits were only evaluated in the first year (2008/2009), but the primocane fruits were evaluated in 2009 and 2010.

General description:

A) Plant:

*Average size information.*—Amara is a thornless, primocane-fruiting blackberry with abundant yields of large, sweet, very firm fruits that show a low rate of regression to red drupelets in post-harvest storage. It is a vigorous and productive variety.

*Growth.*—Plants of Amara have good vegetative vigor and an erect growth habit. New primocanes emerge mainly from the crown and also as suckers from the roots.

*Growth rate.*—The growth rate is medium, with primocanes reaching 40 cm in height within 60 days from emergence.

*Productivity.*—Medium low in the first (primocane crop), but yields are high with each successive floricane and primocane crop cycle. Yields on the first primocane fruiting cycle of a newly planted field are between 0.7 to 1.0 kg per linear meter of row. The floricane crops yield about 2.5 kg of fruit per meter row and the primocane crops (not including the first primocane crop) are between 2.5 and 3.0 kg per meter row.

*Cold hardiness.*—Ultimate cold hardiness is unknown, but in Chile dormant plants have resisted midwinter lows of −7° C. without damage.

*Branching height of the plants.*—Not measured, the plants are always pinched in order to stimulate higher rates of productivity on primocanes.

B) Canes:

*General description.*—Moderately vigorous, erect, no thorns.

*Cane diameter (indicate point of measurement).*—Floricane: Base: 1.62 cm. Midpoint: 0.83 cm. Terminal: 0.55 cm. Mature primocane: Base: 1.62 cm. Midpoint: 0.80 cm. Terminal: 0.50 cm. Internode length: Base: 5.47 cm. Midpoint: 4.65 cm. Terminal: 3.45 cm. Thorn density/30 cm: Base: 0. Midpoint: 0. Terminal: 0.

*Primocane color.*—Base: Background Color: Yellow Green Group 144B overlaid with lines of color in the Grayed-Orange Group 172B. Midpoint: The cane color in the shaded portions is in the Yellow Green Group 144B, however where exposed to sun, the color is in the Greyed-Red 178B. Terminal: Grayed-Red Group 178B.

*Floricane color.*—Base: Greyed-Orange Group 177C. Midpoint: Greyed-Orange Group 177C. Terminal: data not available due to pruning.

*Date of primocane emergence.*—Primocanes begin to emerge during the second week of October (in the southern Hemisphere at 32° 45' S. Lat., 220 m elev.) and continue emerging until the second week of February.

*Date of budbreak.*—Not Measured.

C) Foliage:

*General description.*—Leaves with two to five leaflets, margins are triple-serrate. Petioles and veins, as with the rest of the plant, are thornless.

*Leaves.*—Width: 15.9 cm. Length: 19.4 cm (including petiole). Number of leaflets: 3 to 5 per leaf.

*Leaflet.*—Width: 5.1 cm. Length: 8.8 cm (including petiolules). Margin: Double or triple serrate. Shape: Ovate. Base Adaxial: Green Group 137A in the middle, but the borders of the leaves in the Greyed-Orange Group 166A. Base Abaxial: Green Group 138A. Midpoint Adaxial: Green Group 137B. Midpoint Abaxial: Green Group 138B. Terminal Adaxial: Yellow-Green Group 144A. Terminal Abaxial: Yellow-Green Group 144B.

*Petioles.*—Length: 7.6 cm. Color: Greyed-Red Group 178B.

*Petiolules.*—Length: 0.18-3.4 cm. Color: adaxial side: Greyed-Orange Group 166A. Abaxial side: Yellow-Green Group N144A.

D) Flowers:

*General description.*—There are no material differences noted for flower dimensions and inflorescence characteristics for floricanes compared to primocanes, however floricanes have nearly double the number of flowers on primocane inflorescences and of course the dates of bloom are also different. Therefore, other than the different number of flowers per inflorescence, the characteristics described for the floricane flowers serve for describing those of the primocanes, but bloom times and flower number per cluster for each are noted here:

*Primocane.*—Date of bloom: (Southern Hemisphere). 10% bloom: 25th of December. 50% bloom: 5th of January. Last bloom: 3nd week of January.

*Average number flowers per cluster.*—6.

*Floricane.*—Date of bloom: (Southern Hemisphere) 10% bloom: $12^{th}$ of October. 50% bloom: $25^{th}$ of October. Last bloom: Last week of October.

*Petal color.*—White Group NN155B.

*Reproductive organs.*—Stamens: Erect and numerous. Pistils: Numerous. Pollen: Fertile and abundant. Ovary: Superior.

*Flower diameter.*—2.4-4.7 cm.

*Petal size.*—Width: 1.2 cm. Length: 1.9 cm.

*Average number flowers per cluster.*—11.

*Average number of petals per flower.*—5.

*Peduncle length.*—0.75-2.55 cm.

*Peduncle color.*—Yellow-Green Group 144A.

E) Fruit:

*General description.*—The fruits of Amara are medium to large sized, very firm, very sweet and with very good flavor. They have good black color which is uniform and glossy. The fruits have a low rate of regression to red drupelets in post harvest storage.

*Primocane.*—Average first ripe date: 25th of February in Nogales, Fifth Region of Valparaiso, Chile, which date is about the same time as the ripening date for APF-8 (Prime Jan®) under the same conditions. The primocane harvest lasts for approximately 30 days. Size: Medium to Large (7.6 g on average). Diameter: Equator: 2.27 cm. Base pole: 2.30 cm. Terminal pole: 2.02 cm. Length: 3.04 cm. Shape: broadly oblong to conic shape. Drupelet size: Medium (0.34 cm average). Drupelet skin color: Black Group 203-A. Drupelet flesh color: Greyed-Purple N186-A-B. Seed color: Greyed-Yellow 161-C. Seed size: Small. Firmness: Very Firm. Flavor: Sweet, without bitter aftertaste. Soluble solids: 10.9° Bx. pH: 3.2. Acidity: 0.92. Processed quality: Not evaluated. Uses: Fresh Market. Prickles: None.

*Floricane.*—Average first ripe date: 15th of December in Nogales, Fifth Region of Valparaiso, Chile. This date is approximately 20 days before Navaho. The floricane harvest lasts for about 30 days. Size: Medium (5.7 g on average). Diameter: Equator: 1.92 cm. Base pole: 2.07 cm. Terminal pole: 1.80 cm. Length: 2.6 cm. Shape: Round, somewhat conic. Drupelet size: Medium, 0.34 cm. Drupelet skin color: not measured. Drupelet flesh color: not measured. Seed color: not measured. Seed size: Small. Firmness: Very Firm. Flavor: Sweet, without bitter aftertaste. Soluble solids: 11.2° Bx. pH: Not measured. Acidity: Not measured. Processed quality: Not evaluated. Uses: Fresh Market. Prickles: None.

Thus, in some aspects, the Amara blackberry is characterized by having a primocane fruiting habit on a thornless plant, coupled with high fruit quality (visually attractive with excellent flavor, firmness, and low regression to red drupelets in post harvest). In addition, the productivity is low in the first production cycle (primocanes), typically yielding no more than 1.0 kg per meter of row, but after the first production cycle the productivity increases substantially (2.5 kg or greater per meter row). This may be evidence of a longer juvenile period (that effects productivity) in Amara.

What is claimed is:

1. A new and distinct cultivar of Blackberry plant named 'Amara' as described and shown herein.

* * * * *